United States Patent
Podtaev

(10) Patent No.: US 10,602,933 B2
(45) Date of Patent: Mar. 31, 2020

(54) DIAGNOSING DISORDERS OF MICROVASCULAR TONE REGULATION MECHANISMS

(71) Applicant: Sergei Yurievich Podtaev, Perm (RU)

(72) Inventor: Sergei Yurievich Podtaev, Perm (RU)

(*) Notice: Subject to any disclaimer, the term of this patent is extended or adjusted under 35 U.S.C. 154(b) by 467 days.

(21) Appl. No.: 15/509,637

(22) PCT Filed: Oct. 13, 2014

(86) PCT No.: PCT/RU2014/000765
§ 371 (c)(1),
(2) Date: Mar. 8, 2017

(87) PCT Pub. No.: WO2016/060579
PCT Pub. Date: Apr. 21, 2016

(65) Prior Publication Data
US 2017/0281019 A1    Oct. 5, 2017

(51) Int. Cl.
*A61B 5/02* (2006.01)
*A61B 5/01* (2006.01)
*G16H 50/30* (2018.01)
*G16H 40/63* (2018.01)
*G16H 50/20* (2018.01)
(Continued)

(52) U.S. Cl.
CPC ............ *A61B 5/02007* (2013.01); *A61B 5/01* (2013.01); *A61B 5/4884* (2013.01); *A61B 5/726* (2013.01); *A61B 5/7225* (2013.01); *A61F 7/00* (2013.01); *G16H 40/63* (2018.01); *G16H 50/20* (2018.01); *G16H 50/30* (2018.01); *A61F 2007/0052* (2013.01)

(58) Field of Classification Search
CPC ...... A61B 5/02007; A61B 5/01; G16H 50/30; G16H 50/20; A62B 5/4884
See application file for complete search history.

(56) References Cited

FOREIGN PATENT DOCUMENTS

RU           43967 U1     2/2005
SU         1701277 A1    12/1991

OTHER PUBLICATIONS

Kozlov V.I. er al. Lazernaya dopplerovskaya floumetriya v otsenke sostoianiya i rasstroistv mikrotsirkuliatsii krovi. Rossiisky universitet druzhby narodov, GNTS lazernoi meditsiny. Moscow, 2012, p. 8, line 6—p. 12, line 33, p. 14, lines 1-18.

*Primary Examiner* — Patrick Fernandes
(74) *Attorney, Agent, or Firm* — Nadya Reingand; Yan Hankin

(57) ABSTRACT

The invention relates to registering changes in vascular tone during and after a functional load, and processing data using spectral analysis methods within the frequency ranges of endothelial (0.0095-0.02 Hz), neurogenic (0.02-0.05 Hz), and myogenic (0.05-0.14 Hz) regulation mechanisms. Furthermore, the temperature of an area of a patient's skin is continuously registered. During the first 1-2 minutes, the temperature of the examined skin surface is increased to 38-42° C., and the heating power is fixed. Temperature fluctuations are registered over the course of 10 minutes. The heater is shut-off. Over the course of 10 minutes following the shut-off and a decrease in temperature to 30-32° C., temperature fluctuations continue to be registered, and the obtained values are compared, with coefficients being calculated for the relative change in the amplitudes of the temperature fluctuations, which are then used for determining the existence of a disorder in a vascular tone regulation mechanism.

4 Claims, 2 Drawing Sheets

Figure 1:
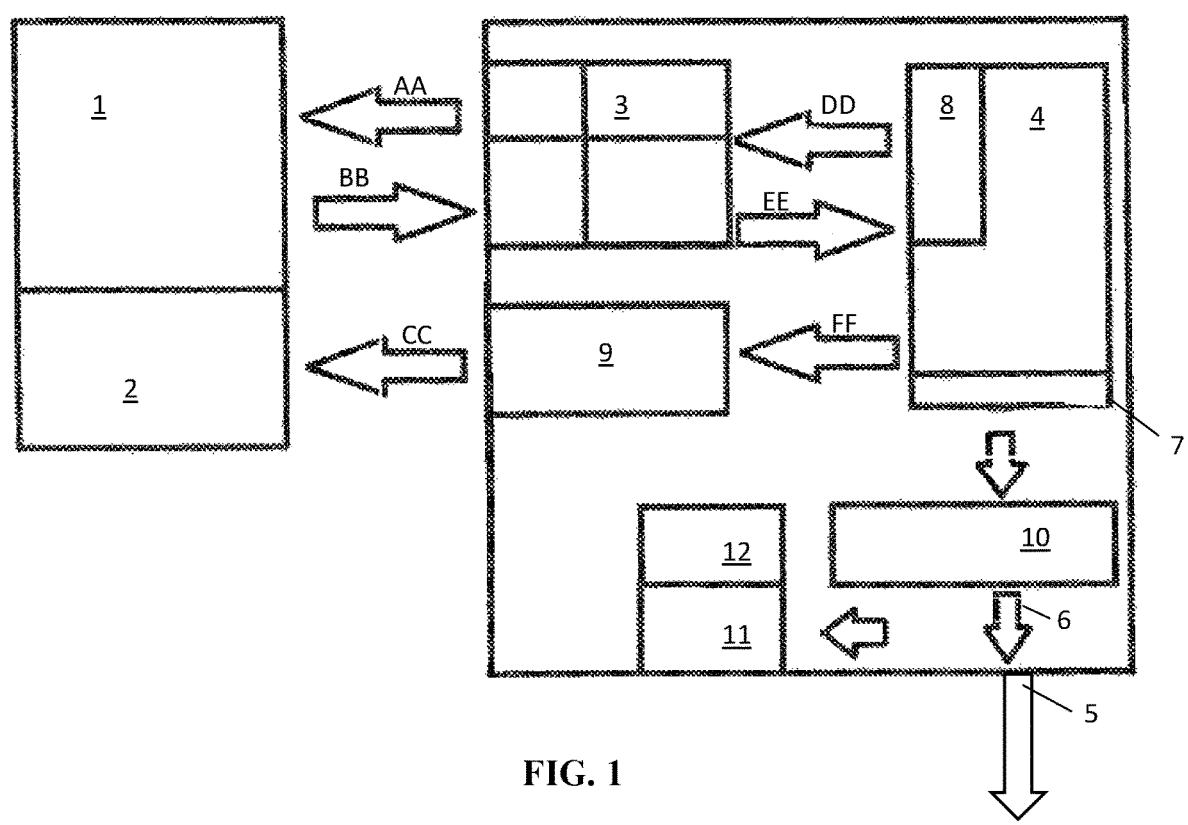

(51) Int. Cl.
*A61B 5/00* (2006.01)
*A61F 7/00* (2006.01)

`US 10,602,933 B2`

DIAGNOSING DISORDERS OF MICROVASCULAR TONE REGULATION MECHANISMS

CROSS-REFERENCE TO RELATED APPLICATIONS

The present application is the National stage application from PCT application PCT/RU2014/000765 filed Oct. 13, 2014.

FIELD OF THE INVENTION

This invention relates to medicine, and more in particular to functional diagnostics, and can be used for diagnosing dysfunctions of the endothelial, neurogenic and myogenic mechanisms of microvascular tone regulation.

DESCRIPTION OF PRIOR ART

Prior art provides a method for assessing artery reactivity in patient (U.S. Pat. No. 8,551,008 published on 8 Oct. 2013) which comprises:

initiating vasodilating stimulation in the patient, occluding artery blood flow to a selected part of the patient's body using one or more occluding cuffs so that to stimulate the artery occlusion of a selected region of such part of the patient's body, simultaneous monitoring of the patient's skin temperature in one (selected) and another (control) regions before, during and after the artery occlusion, prior to attainment of the equilibrium temperature with the use of temperature measuring device which does not exert any considerable calorific power, and positive or negative pressure to the skin surface; in this case, the above regions are on the contralateral parts of the body; and measuring initial temperature in the first (i.e. selected) region before the artery occlusion;

measuring the maximum temperature in the first region after the artery occlusion; and evaluating artery reactivity in the patient based upon changes in the temperature in the second (i.e. control) region and upon reversal temperature change related to the above initial temperature and maximum temperature in the first region of the body.

The disadvantages of the method are long running process and inadequate sustainability and reliability of the diagnostic results.

From the prior art we are aware of a method for evaluating the diagnostics of the endothelial, neurogenic and myogenic mechanisms of vascular tone regulation through recording oscillations of skin blood flow by an ultrasound Doppler flowmeter (such as LAKK-01 produced by LAZMA Research and Production Enterprise, Russia).

To evaluate the condition of the endothelial, neurogenic and myogenic mechanisms of vascular tone regulation it is necessary to perform a hot caloric test and, to that end, to heat the skin surface under study from 32° up to 45° C., to record the microcirculation indicator expressed in perfusion units and to make spectral analysis of LDF-gram (The Laser Doppler Flowmetry of Blood Microcirculation/Edited by A. I. Krupatkin, V. V. Sidorov: Guide for Medical Practitioners.—M.: Meditzina Publishing House OJSC, 2005-256 p.).

The disadvantages of this method includes the need for expensive equipment, low reproducibility of measurements resulting from heterogeneous spatial distribution of blood vessels in the true skin and a great number of artifacts associated with the light guide microdisplacements with respect to the scanned surface in the process of measurement, that significantly reduces the accuracy of analysis of low frequency oscillations corresponding to the endothelial, neurogenic and myogenic mechanisms of microvascular tone regulation.

It is known in the prior art to provide an electronic temperature recorder that incorporates external temperature sensors connected to the first master input of an A/D-converter, internal temperature sensors connected to the second master input of the A/D-converter, and a conversion and comparison unit connected to the A/D-converter, a non-volatile memory module, a display, a keyboard and a coupler (interface unit) which output is connected to the PC connection ter urinal (RU 21092 U1, 2001).

Such temperature recorder provides relatively high accuracy of multichannel measurements in a wide temperature range, and high reliability of information obtained. However its functionality is still insufficient. In particular, it does not allow efficient analysis results of control over condition of the objects highly sensitive to changes in environment temperature, such as donated blood, organs, medicines and vaccines.

The closest prior art is the electronic temperature recorder that incorporates external temperature sensors connected to the first master input of an A/D-converter, internal temperature sensors connected to the second master input ofthe A/D-converter, and a conversion and comparison unit connected to the A/D-converter, a non-volatile (EEPROM) memory module, a display, a keyboard and a coupler (interface unit) which output is connected to a PC connection terminal, and an internal power supply with a constant-voltage regulator connected to the output connection of the external power supply which additionally comprises a scan signal generator having an input coupled to the corresponding output of the conversion and comparison unit, and an output coupled to the control input connector of the A/D converter, the output connection access detector and the control connector of the external temperature sensors that are connected via a switchboard to the conversion and comparison unit, a temperature sensor coupled to an additional input of the A/D converter, and a setting storage unit, a main memory unit and a real-time clock, all three connected to the conversion and comparison unit, while the PC connection teiminal enables the connection of a theimal printer (RU 43967 U1, 2005).

Such temperature recorder provides relatively high accuracy of multichannel measurements in a wide temperature range, and high reliability of information obtained. However the instrument is assembled with the parts that became obsolete long time ago. Besides, it uses outdated communications interface (RS-232) with the personal computer (hereinafter referred to as the PC).

SUMMARY OF THE INVENTION

The proposed invention achieves the object of improving the accuracy and reliability of analysis, and simplifying the process through using the electronic temperature recorder.

To the accomplishment of the above object, the invention has the attributes set forth in claim 1, which are common with the prototype, such as the method for diagnosing dysfunctions of the endothelial, neurogenic and myogenic mechanisms of vascular tone regulation by recording changes in vascular tone during and after functional load, processing of data with the help of mathematical methods of spectral analysis in the frequency ranges corresponding the endothelial (0.0095-0.02 Hz), neurogenic (0.02-0.05 Hz) and myogenic (0.05-0.14 Hz) mechanisms of regulation of vascular tone and essential distinctive attributes, such as continuous recording of temperature on the tested portion of the patient's skin by a temperature recorder, increasing the skin surface temperature up to 38-42° C. within the first 1-2 minutes, setting of the mode of permanent thermal power with recording of temperature oscillations within not less than 10 minutes after the beginning of the hot thermal test, followed by deactivating the heating and resuming the recording when the temperature reduces to 30-32° C., but not later than 10 minutes after, and comparing the values recorded, and calculating the coefficients of relative change in the amplitude of oscillations of skin temperature, which indicate a dysfunction ofthe mechanism of vascular tone regulation.

According to claim 2, the coefficients of relative change in the amplitude of oscillations of skin temperature are calculated using the following formulas:

$$A=(A_1-A_0)/A_0$$

$$B=(B_1-B_0)/B_0.$$

$$C=(C_1-C_0)/C_0$$

where $A_0B_0C_0$—amplitudes of oscillations of skin temperature in the endothelial, neurogenic and myogenic frequency ranges after the completion of hot thermal test, respectively;

$A_1B_1C_1$—average amplitudes of oscillations of skin temperature in the endothelial, neurogenic and myogenic frequency ranges during the hot thermal test, respectively, when A coefficient lower than 0.7 indicates a dysfunction of the endothelial mechanism of vascular tone regulation, B coefficient lower than 1.1 indicates a dysfunction ofthe neurogenic mechanism of vascular tone regulation, and C coefficient lower than 1.3 indicates a dysfunction of the myogenic mechanism of vascular tone regulation.

According to claim 3, the temperature is measured at the frequency of at least 1 Hz.

According to claim 4, the received signals of temperature values are processed with the use of computer software through wavelet analysis.

The above aggregation of the essential attributes of the method ensures the technical result which is improved accuracy and simplified method for diagnosing dysfunctions of the endothelial, myogenic and neurogenic mechanisms of vascular tone regulation.

The object is accomplished through the attributes specified in claim 5, such as the electronic temperature recorder used to embody the method described in claim 1, which consists of an external temperature sensor equipped with a heating unit connected to the first channel of microchip of A/D converter which is coupled with the microcontroller that transmits data to a PC via an interface, when one chip ofthe microchip of A/D convertercomprises a three-channel multiplexer, an instrumentation amplifier, a reference voltage source, a temperature sensor, controlled current source and sigma-delta converter itself; the microcontroller comprises a Flash memory, main memory unit, non-volatile memory (EEPROM), a UART interface for communications with the PC, and a SPI interface to communicate with the A/D converter; and the temperature recorder comprises an optoisolator between the heating unit and the measuring circuit, and an optoisolator between the measuring circuit and the PC signal, and the power supply together with a galvanic isolation unit; and the external temperature sensor comprises a bridge measuring circuit with a thermistor that makes it possible to get rid of common mode noise at the A/D converterinput as well as a heating unit based on the SMD-resistors for thermal effects on the patient's skin.

According to claim 6, the logic of work and data storage are implemented by the external software installed on the PC.

The above aggregation of the essential attributes of the method ensures the technical result which is improved accuracy and simplified method for diagnosing dysfunctions of the endothelial, myogenic and neurogenic mechanisms of microvascular tone regulation.

This invention may be embodied in the form illustrated in the accompanying examples and schematic block diagram of the electronic temperature recorder.

Description of the Preferred Embodiment

The method is embodied as follows (See FIG. 2). The patient's temperature is continuously measured 101, e.g., on a fingertip of the patient with the use of the electronic temperature recorder (see FIG. 1). The heating unit is turned on, and increases the temperature of the tested skin surface up to 40° C. within 1-2 minutes 102, and the signal is recorded for at least 10 minutes once a mode of permanent thermal power is stabilized 103, and for at least 10 minutes after the heating is turned off and the temperature reduces 104. The temperature is measured at a frequency of at least 1 Hz. The received signals of temperature values are processed with the use of computer software through wavelet analysis 105. The amplitude of skin temperature oscillations is calculated in the frequency ranges corresponding the endothelial (0.0095-0.02 Hz), neurogenic (0.02-0.05 Hz) and myogenic (0.05-0.14 Hz) mechanisms of regulation of vascular tone 106 within the first 10 minutes of the initial conditions and then within 10 minutes after the completion of the hot thermal test.

The coefficients are calculated using the following formulas:

$$A=(A_1-A_0)/A_0$$

$$B=(B_1-B_0)/B_0.$$

$$C=(C_1-C_0)/C_0$$

where $A_0B_0C_0$—amplitudes of oscillations of skin temperature in the endothelial, neurogenic, and myogenic frequency ranges after the hot thermal test, respectively, within 10 minutes after the completion of the hot thermal test;

$A_1B_1C_1$—average amplitudes of oscillations of skin temperature in the endothelial, neurogenic and myogenic frequency ranges during the hot thermal test, respectively, within 10 minutes during the hot thermal test. Indication of a dysfunction 107 is performed based on the values outputted and as follows:

A coefficient lower than 0.7 indicates a dysfunction of the endothelial mechanism of vascular tone regulation, B coefficient lower than 1.1 indicates a dysfunction of the neurogenic mechanism of vascular tone regulation, and C coefficient lower than 1.3 indicates a dysfunction of the myogenic mechanism of vascular tone regulation 108.

EXAMPLES OF SPECIFIC EMBODIMENT OF THE METHOD

Example 1

Volunteer E Aged 28 Years, Healthy

The sensor of temperature recorder was put on the index fingertip of the volunteer. The recorder was turned on to record the skin temperature continuously within 10 minutes during the hot thermal test and within 10 minutes after the recorder was turned off and the temperature reduced. The measurements were taken at the frequency at least 1 Hz. The received signal of temperature values was processed with the use of computer software through wavelet analysis to get wavelet spectrograms. The mean-square amplitude of oscillations in the range of 0.0095-0.02 Hz was calculated within 10 minutes after the completion of hot thermal test ($A_0=1.42*10^{-2\circ}$ C.), and within 10 minutes during the hot thermal test ($A_1=2.44*10^{-2\circ}$ C.), after which A coefficient was calculated with the formula: $A=(2.44-1.42)/1.42=0.72$. The oscillation amplitude in the range of 0.02-0.05 Hz was calculated within 10 minutes after the completion of the hot thermal test ($B_0=0.64*10^{-2\circ}$ C.), and within 10 minutes during the hot thermal test ($B_1=3.45*10^{-2\circ}$ C.), after which B coefficient was calculated with the formula: $B=(3.45-0.64)/0.64=4.39$. The oscillation amplitude in the range of 0.05-0.14 Hz was calculated within 10 minutes after the completion of the hot thermal test ($C_0=0.19*10^{-2\circ}$ C.), and within 10 minutes during the hot thermal test ($C_1=0.99*10^{-2\circ}$ C.), after which C coefficient was calculated with the formula: $C=(0.99-0.19)/0.19=4.21$.

A coefficient equaled 0.72 that was higher than 0.7 which indicated the freedom from any dysfunction of the endothelial mechanism of vascular tone regulation. B coefficient equaled 4.39 that was higher than 1.1 which indicated that the volunteer had no dysfunction of the neurogenic mechanism of vascular tone regulation. C coefficient was 4.21, i.e. higher than 1.3, which proved that there was no dysfunction of the myogenic mechanism of vascular tone regulation.

Example 2

Patient V. aged 55 years, DS: diabetes mellitus type 2, not compensated. Non-proliferative diabetic rentinopathy of both eyes. Dyslipidemia. Non-alcoholic fatty liver disease. Distal diabetic neuropathy of lower extremities. Hypertensive disease, II degree, risk 4.

The sensor of temperature recorder was put on the index fingertip of the volunteer. The recorder was turned on to record the skin temperature continuously within 10 minutes during the hot thermal test and within 10 minutes after the recorder was turned off and the temperature reduced. The measurements were taken at the frequency at least 1 Hz. The received signal of temperature values was processed with the use of computer software through wavelet analysis to get wavelet spectrograms. The mean-square amplitude of oscillations in the range of 0.0095-0.02 Hz was calculated within 10 minutes after the completion of hot thermal test ($A_0=0.67*10^{-2\circ}$ C.), and within 10 minutes during the hot thermal test ($A_1=0.72*10^{-2\circ}$ C.), after which A coefficient was calculated with the formula: $A=(0.72-0.67)/0.67=0.07$. The oscillation amplitude in the range of 0.02-0.05 Hz was calculated within 10 minutes after the completion of the hot thermal test ($B_0=0.16*10^{-2\circ}$ C.), and within 10 minutes during the hot thermal test ($B_1=0.15*10^{-2\circ}$ C.), after which B coefficient was calculated with the formula: $B=(0.15-0.16)/0.16=-0.06$. The oscillation amplitude in the range of 0.05-0.14 Hz was calculated within 10 minutes after the completion of the hot thermal test ($C_0=0.09*10^{-2\circ}$ C.), and within 10 minutes during the hot thermal test ($C_1=0.11*10^{-2\circ}$ C.), after which C coefficient was calculated with the formula: $C=(0.11-0.09)/0.09=0.22$.

A coefficient equaled 0.07 that was lower than 0.7 which indicated the presence of dysfunction of the endothelial mechanism of vascular tone regulation. B coefficient equaled −0.06 that was lower than 1.1 which indicated that the patient had dysfunction of the neurogenic mechanism of vascular tone regulation. C coefficient was 0.22, i.e. lower than 1.3, which proved that there was dysfunction of the myogenic mechanism of vascular tone regulation.

The result was confirmed by the results of biochemical blood test: the content of triglycerides (2.4 mmol/l), cholesterol (5.66 mmol/L), LDL (3.03 mmol/L) and glycated hemoglobin (11.4%) was increased. Therefore, the conclusion of neurologist was: metabolic neuropathy.

Example 3

Patient Sh. aged 50 years, DS: diabetes mellitus type 2, requiring insulin therapy, not compensated. Retinal angiopathy of both eyes. Distal diabetic neuropathy of lower extremities. Steatohepatitis of mixed origin (toxic, medicinal and diabetic). Dyslipidemia. Myocardiodystrophy. Hypertensive disease, II degree, risk 4.

The sensor of temperature recorder was put on the index fingertip of the volunteer. The recorder was turned on to record the skin temperature continuously within 10 minutes during the hot thermal test and within 10 minutes after the recorder was turned off and the temperature reduced. The measurements were taken at the frequency at least 1 Hz. The received signal of temperature values was processed with the use of computer software through wavelet analysis to get wavelet spectrograms. The mean-square amplitude of oscillations in the range of 0.0095-0.02 Hz was calculated within 10 minutes after the completion of hot thermal test ($A_0=2.1*10^{-2\circ}$ C.), and within 10 minutes during the hot thermal test ($A_1=2.83*10^{-2\circ}$ C.), after which A coefficient was calculated with the formula: $A=(2.83-2.1)/2.1=0.35$. The oscillation amplitude in the range of 0.02-0.05 Hz was calculated within 10 minutes after the completion of the hot thermal test ($B_0=0.85*10^{-2\circ}$ C.), and within 10 minutes during the hot thermal test ($B_1=1.25*10^{-2\circ}$ C.), after which B coefficient was calculated with the formula: $B=(1.25-0.85)/0.85=0.47$. The oscillation amplitude in the range of 0.05-0.14 Hz was calculated within 10 minutes after the completion of the hot thermal test ($C_0=0.26*10^{-2\circ}$ C.), and within 10 minutes during the hot thermal test ($C_1=0.28*10^{-2\circ}$ C.), after which C coefficient was calculated with the formula: $C=(0.28-0.26)/0.264.08$.

A coefficient equaled 0.35 that was lower than 0.7 which indicated the presence of dysfunction of the endothelial mechanism of vascular tone regulation. B coefficient equaled 0.47 that was lower than 1.1 which indicated that the patient had dysfunction of the neurogenic mechanism of vascular tone regulation. C coefficient was 0.08, i.e. lower than 1.3, which proved that there was dysfunction of the myogenic mechanism of vascular tone regulation.

The result was confirmed by the results of biochemical blood test: the content of triglycerides (2.7 mmol/l), cholesterol (6.65 mmol/L), LDL (3.91 mmol/L) and glycated hemoglobin (11.4%) was increased. Therefore, the conclusion of neurologist was: metabolic neuropathy of lower extremities.

The indicators of the endothelial, myogenic and neurogenic mechanisms of vascular tone regulation in three healthy volunteers were compared with those in three diabetic patients.

The results are presented in Table 1 and Table 2.

TABLE 1

Amplitudes of skin temperature oscillations ($*10^{2\circ}$ C.) and coefficient of their relative changes in healthy volunteers

| ## | Volunteer | Endothelial 0.0095-0.02 Hz | | | Neurogenic 0.02-0.05 Hz | | | Myogenic 0.05-0.14 Hz | | |
|---|---|---|---|---|---|---|---|---|---|---|
| | | $A_0$ | $A_1$ | A | $B_0$ | $B_1$ | B | $C_0$ | $C_1$ | C |
| 1. | E | 1.42 | 2.44 | 0.72 | 0.64 | 3.45 | 4.39 | 0.19 | 0.99 | 4.21 |
| 2. | Sh | 1.73 | 3.11 | 0.80 | 0.79 | 2.23 | 1.82 | 0.27 | 1.07 | 2.96 |
| 3. | Ch | 1.96 | 7.11 | 2.63 | 1.22 | 3.41 | 1.80 | 0.15 | 0.70 | 3.67 |

Table 1.

In healthy volunteers, A coefficient ranged from 0.72 to 2.63, B coefficient varied from 1.80 to 4.39, and C coefficient fluctuated between 2.96 and 4.21.

TABLE 1

Amplitudes of skin temperature oscillations ($*10^{2\circ}$ C.) and coefficient of their relative changes in diabetic patients

| ## | Patient | Endothelial 0.0095-0.02 Hz | | | Neurogenic 0.02-0.05 Hz | | | Myogenic 0.05-0.14 Hz | | |
|---|---|---|---|---|---|---|---|---|---|---|
| | | $A_0$ | $A_1$ | A | $B_0$ | $B_1$ | B | $C_0$ | $C_1$ | C |
| 1. | V | 0.67 | 0.72 | 0.07 | 0.16 | 0.15 | −0.06 | 0.09 | 0.11 | 0.22 |
| 2. | Sh | 2.1 | 2.83 | 0.35 | 0.85 | 1.25 | 0.47 | 0.26 | 0.28 | 0.08 |
| 3. | Shch | 2.28 | 2.33 | 0.02 | 1.42 | 2.28 | 0.61 | 0.73 | 1.5 | 1.05 |

Table 2.

In diabetic patients, A coefficient ranged from 0.02 to 0.35, B coefficient varied from 0.06 to 0.61, and C coefficient fluctuated between 0.08 and 1.05.

The values of coefficients in all frequency ranges in the diabetic patients were significantly lower than those in healthy volunteers.

The advantages of the proposed method are increased sensitivity due to the exact threshold, convenience and high-speed performance, high reproducibility of results, simplified procedure of study due to the lack of artifacts associated with the light guide microdisplacements with respect to the scanned surface in the process of measurement, and low cost.

DESCRIPTION OF DRAWING TO ILLUSTRATE THE INVENTION

The drawing shows a schematic block diagram of a preferred embodiment of the electronic temperature recorder.

Figure 2:
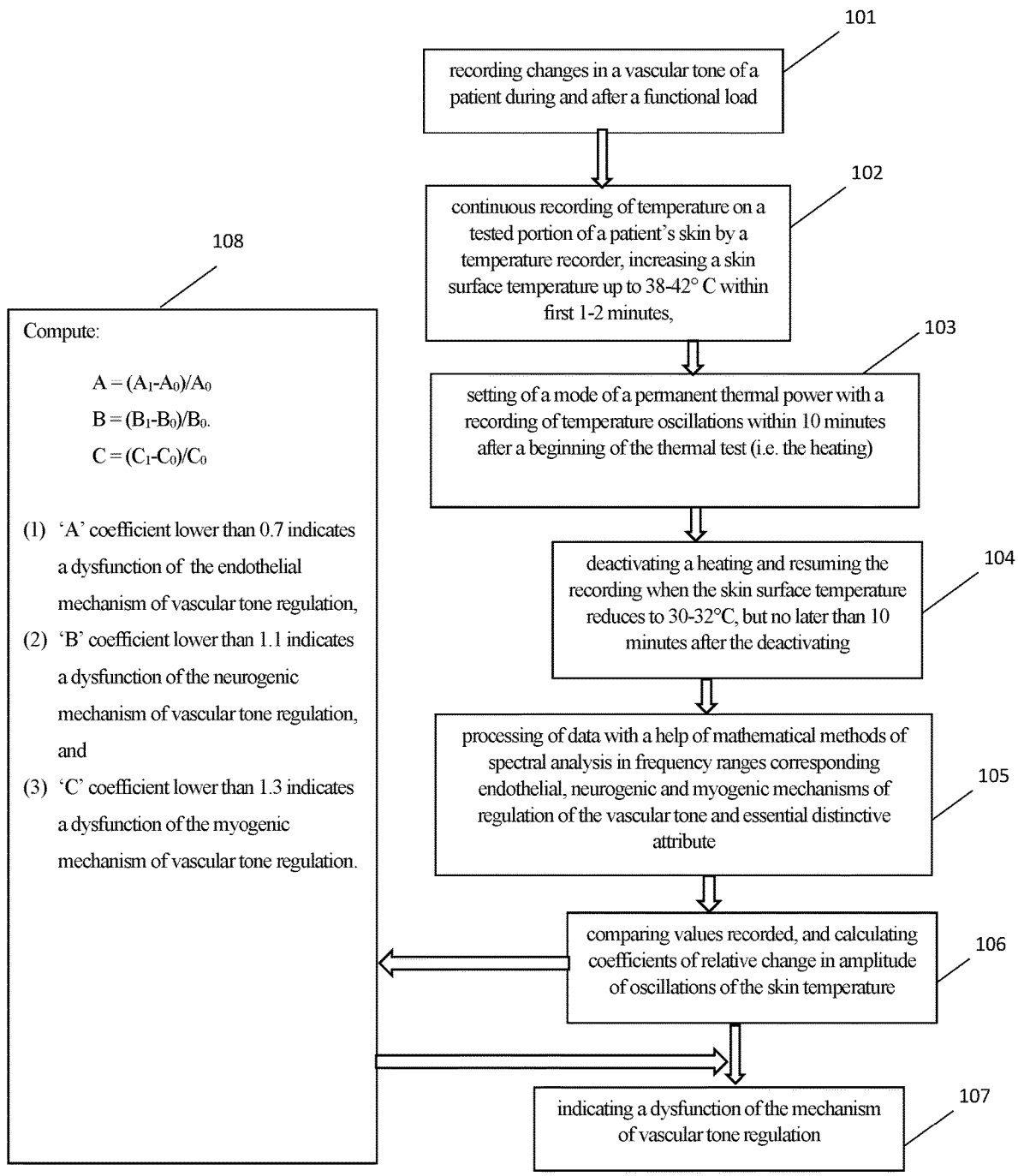

FIG. 1 shows: 1—Temperature sensor; 2—Heater; 3—Analog-to-digit converter; 4—Microcontroller; 5—To PC; 6—Interface; 7—UART interface; 8—SPI interface; 9—Optocoupler; 10—Optocoupler+FT232; 11—Power supply unit; 12—Galvanic isolation; AA—Current; BB—Signal; CC—Pulse-width modulation; DD—Control; EE—Data; FF—Pulse width modulation.

Description of interconnection between elements and units (FIG. 1): The electronic temperature recorder used to embody the method consists of an external temperature sensor connected to A/D converter 3 which transmits the data to the PC. The output of external temperature sensor 1 is coupled to the measuring channel of microchip of A/D converter 3, and the microchip output is coupled to SPI 8 of microcontroller 4 which output is connected to the input of PC5 via USB interface 6. The first output of microcontroller 4 is connected to the control input of A/D converter 3 via SPI 8. The second output of microcontroller 4 is connected to input of heating unit 2 of temperature sensor 1 via optocoupler 9. The third output of microcontroller 4 is connected to PC5 via interface 7 and optocoupler 10. The device is powered via USB and PC5 via power supply unit 11 and galvanic isolation unit 12.

The measuring part of the recorder is based on the AD7793 microchip produced by Analog devices. One chip of A/D converter 3 comprises three-channel multiplexer, instrumentation amplifier, reference voltage source, temperature sensor, controlled current source and sigma-delta converter itself.

Microcontroller 4 comprises Flash memory, main memory unit, non-volatile memory (EEPROM), UART7 for communications with the PC5 and SPI8 for communications with A/D converter 3.

The Recorder Operates as Follows:

The signal of sensor 1 is transmitted to the input switchboard, and then—to the instrumentation amplifier. Then the amplified signal is sent to the A/D converter 3. The result of the conversion is read by the microcontroller 4. The microcontroller 4 controls the analog-to-digital converter and the input switch. The microcontroller 4 also performs primary processing, and serves as interface with the control and display unit. The circuit comprises a current stabilizer to feed bridge temperature sensors. The A/D converter unit is designed as a separate measuring substrate. The substrate is galvanically isolated from the measuring circuits connected to the control and display unit.

The measuring part of the recorder is based on the AD7793 microchip produced by Analog devices. One chip comprises three-channel multiplexer, instrumentation amplifier, reference voltage source, temperature sensor, controlled current source and sigma-delta converter. The main advantage of this scheme is its high accuracy. The AD7793 microchip of the A/D converter has rather high resolution (24-bit) that allows for measurements accurate to a thousandth of a degree at the frequency of 128 Hz. Besides, in order to suppress the noise in the sensor the bridge measurement circuit is used, which contributes to suppression of common mode noise. The built-in multiplexer allows for simultaneous measurements for three channels. Due to the fact that all channels of the A/D converter and reference voltage source are on the same chip, they have very similar characteristics when used in the same process, which makes it possible to minimize temperature drift in the measuring part. In most cases, the primary analog signals taken from the thermistors are represented in millivolts. The use the switchboard for immediate switching of weak signals can serve as a source of noise, interference, and temperature drifts. The fact that amplifier in the AD7793 microchip is located before the power switching unit also positively affects the accuracy.

The AD7793 microchip made it possible to avoid the use of such elements as temperature sensor of conversion and comparison unit, switchboard, analog-digital converter, and conversion and comparison unit comparing the conversion unit.

All periphery of the recorder is controlled the ATmega168 microcontroller. The microcontroller allowed us to avoid the use of a number of components, such as setting storage unit, main memory unit, scan signal generator, and encoder.

The Electronic Temperature Recorder Makes it Possible:

To record the temperature oscillations of the object under test with a temperature resolution to 0.001° and frequency up to 128 Hz.

To heat the object under test up to 45° C.

To transmit data to the PC using special software (hereinafter the Software) which allows for their storage, processing and display on plot.

To take control commands from the software, such as: "Change the heating power", "Save/read the calibration coefficients in the microcontroller memory", and "Change the conversion frequency".

The operation of the recorder together with the software made it possible to avoid the use of such elements as: real-time clock, display, keyboard and encoder. As a result of the deployment of the up-do-date components (microcontroller, ADC) in conjunction with external software installed on the PC allows for significant reduce the number of functional units in the electrical circuit by shifting a part of functionality to the software, as well as to simplify and accelerate the process of its eventual improvements.

INDUSTRIAL APPLICABILITY

The group of inventions relates both to medicine and measuring equipment, and can be advantageously used for registration of patient's skin temperature oscillations for medicinal purposes. The recorder can be made of the available components at the assembly site of instrument-making enterprises. Both method and recorder used for its embodiment will be widely used in medical practice.

What is claimed is:

1. A method for diagnosing dysfunctions of an endothelial mechanism of vascular tone regulation, a neurogenic mechanism of vascular tone regulation, and/or a myogenic mechanism of vascular tone regulation, comprising:
   one or more processors and/or devices performing steps of:
      recording changes in a patient's vascular tone during and after a functional load,
      processing of data via employing mathematical methods of spectral analysis in frequency ranges corresponding to endothelial, neurogenic, and myogenic mechanisms of regulation of the vascular tone and attributes of the vascular tone,
      continuously recording of a patient's temperature on a tested portion of a patient's skin by a temperature recorder,
      heating a part of the patient, the heating comprising increasing a skin surface temperature up to 38-42 C within 1-2 minutes of a beginning of the heating,
      setting of a mode of permanent thermal power and performing a recording of temperature oscillations for at least 10 minutes once the mode of permanent thermal power is set,
      the heating being followed by a deactivating of the heating and resuming the recording of temperature oscillations for at least 10 minutes while the skin surface temperature reduces to,
      comparing values recorded, and
      calculating coefficients of relative change in an amplitude of recorded temperature oscillations, the coefficients indicating whether a dysfunction of one or more mechanisms of vascular tone regulation exists.

2. The method of claim 1, wherein the coefficients of relative changes in the amplitudes of the skin surface temperature are:

$$A=(A_1-A_0)/A_0, B=(B_1-B_0)/B_0, \text{ and } C=(C_1-C_0)/C_0,$$

where $A_0$, $B_0$, and $C_0$ are amplitudes of the oscillations of the skin surface temperature in the endothelial, neurogenic, and myogenic frequency ranges, respectively, after deactivating of the heating;
   where $A_1$, $B_1$, and $C_1$ are average amplitudes of the oscillations of the skin surface temperature in the endothelial, neurogenic, and myogenic frequency ranges during the heating,
   where an A coefficient lower than 0.7 indicates a dysfunction of the endothelial mechanism of vascular tone regulation, a B coefficient lower than 1.1 indicates a dysfunction of the neurogenic mechanism of vascular tone regulation, and a C coefficient lower than 1.3 indicates a dysfunction of the myogenic mechanism of vascular tone regulation.

3. The method of claim 1, wherein the skin surface temperature is measured at a frequency of at least 1 Hz.

4. The method of claim 1, wherein temperature values are processed via a wavelet analysis.

* * * * *